(12) United States Patent
Butterfield et al.

(10) Patent No.: US 11,850,395 B2
(45) Date of Patent: Dec. 26, 2023

(54) SYRINGE DRIVER FOR INFUSION

(71) Applicant: CareFusion 303, Inc., San Diego, CA (US)

(72) Inventors: Robert Dwaine Butterfield, Poway, CA (US); Mark Bloom, Chula Vista, CA (US); Daniel Abal, San Diego, CA (US); Kevin Gregory Carothers, Memphis, TN (US)

(73) Assignee: CAREFUSION 303, INC., San Diego, CA (US)

( * ) Notice: Subject to any disclaimer, the term of this patent is extended or adjusted under 35 U.S.C. 154(b) by 212 days.

(21) Appl. No.: 15/982,973

(22) Filed: May 17, 2018

(65) Prior Publication Data
US 2019/0351131 A1   Nov. 21, 2019

(51) Int. Cl.
*A61M 5/145* (2006.01)
*A61M 5/142* (2006.01)
(Continued)

(52) U.S. Cl.
CPC ........ *A61M 5/1456* (2013.01); *A61M 5/1458* (2013.01); *A61M 5/14216* (2013.01); *A61M 5/16854* (2013.01); *A61M 5/3287* (2013.01)

(58) Field of Classification Search
CPC ................ A61M 5/1456; A61M 5/142; A61M 2005/14513; A61M 5/145;
(Continued)

(56) References Cited

U.S. PATENT DOCUMENTS

| 4,398,542 A | 8/1983 | Cunningham et al. |
| 4,898,578 A * | 2/1990 | Rubalcaba, Jr. ...... A61M 5/172 |
| | | 700/83 |

(Continued)

FOREIGN PATENT DOCUMENTS

| CN | 105188796 A | 12/2015 |
| EP | 1349596 A1 | 10/2003 |

(Continued)

OTHER PUBLICATIONS

International Search Report and Written Opinion for Application No. PCT/US2019/031354, dated Jul. 10, 2019, 16 pages.
(Continued)

*Primary Examiner* — Katherine H Schwiker
*Assistant Examiner* — Anna E Goldberg-Richmeier
(74) *Attorney, Agent, or Firm* — Morgan, Lewis & Bockius LLP

(57) ABSTRACT

A syringe pump can be operated to produce fluid flow from a syringe installed therein. Features of the pump can produce a desired rapid commencement of flow followed by smooth delivery uninterrupted by stiction-induced slowing and acceleration. A stiff drivetrain can facilitate detection of excessive forces indicative of friction at a stopper-wall interface. The motor drive, gearing, and control parameters can enable customized acceleration patterns to determine optimal initial stage advancement to provide fluid delivery. These patterns can minimize or eliminate the delay in commencement of flow by overcoming both mechanical slack remaining and syringe stopper slack. To avoid flow irregularities produced by stiction forces in the stopper further, a mechanical vibration can be provided to the syringe and/or barrel to introduce movement of the stopper-wall interface, reducing the creation of high static friction coefficients.

20 Claims, 10 Drawing Sheets

(51) Int. Cl.
*A61M 5/168* (2006.01)
*A61M 5/32* (2006.01)

(58) Field of Classification Search
CPC .......... A61M 5/16831; A61M 5/16854; A61M 5/20; A61B 2018/0088
See application file for complete search history.

(56) References Cited

U.S. PATENT DOCUMENTS

| | | | |
|---|---|---|---|
| 5,647,851 A | 7/1997 | Pokras | |
| 2003/0229311 A1* | 12/2003 | G. Morris | A61M 5/1458 604/151 |
| 2007/0058412 A1* | 3/2007 | Wang | A61M 5/16809 365/120 |
| 2012/0071828 A1* | 3/2012 | Tojo | A61J 1/2096 604/131 |
| 2013/0184641 A1* | 7/2013 | Li | A61M 5/172 604/67 |
| 2017/0056636 A1* | 3/2017 | Shadduck | A61M 1/0084 |
| 2020/0276391 A1* | 9/2020 | Ebner | A61M 5/3202 |

FOREIGN PATENT DOCUMENTS

| | | | | |
|---|---|---|---|---|
| JP | 2003511104 A | 3/2003 | | |
| JP | 2010501286 A | 1/2010 | | |
| KR | 20060121916 A | 11/2006 | | |
| WO | WO-2018033490 A1 | * 2/2018 | .......... A61M 5/1456 |
| WO | WO-2019081518 A1 | * 5/2019 | ........ A61M 5/31513 |
| WO | WO-2019183098 A1 | * 9/2019 | .............. A61M 5/31 |

OTHER PUBLICATIONS

Chinese Office Action for Application No. 201980031727.7, dated Apr. 19, 2022, 13 pages including translation.
Korean Office Action for Application No. 10-2020-7034034, dated Aug. 24, 2022, 8 pages including translation.
European Office Action for Application No. 19725562.3, dated Jun. 5, 2023, 4 pages.
Japanese Office Action for Application No. 2020-564415, dated Feb. 14, 2023, 7 pages including translation.
Japanese Office Action for Application No. 2020-564415, dated Sep. 8, 2023, 7 pages including translation.

* cited by examiner

SYRINGE DRIVER FOR INFUSION

FIELD

The present disclosure is related generally to drive mechanisms for medical infusion pumps, and more particularly, to systems and methods for driving the plunger of a syringe in a syringe pump.

BACKGROUND

The infusion of medical fluids, such as parenteral fluids, into the human body is accomplished in many cases by means of a syringe pump in which a syringe containing the parenteral fluid is mounted. Syringe pumps typically secure the barrel in a fixed position and push or "drive" the plunger into the barrel at a controlled rate to expel the fluid. A fluid administration set conducts the expelled fluid from the barrel to the patient. Many syringe pumps have a threaded lead screw rotated by a motor and a screw drive mechanism such as a split nut that translates the rotational motion of the lead screw into linear motion. A driver linkage is connected to the screw drive mechanism and to the plunger for driving the plunger into the barrel in accordance with the movement of the lead screw to expel the parenteral fluid.

SUMMARY

The subject technology is illustrated, for example, according to various aspects described below. These are provided as examples and do not limit the subject technology.

An infusion system can include: a receptacle for receiving a syringe, the syringe comprising a barrel and a plunger having a stopper; a drive head for advancing the plunger within the barrel; and a vibration device for applying mechanical vibration between the barrel and the plunger.

The infusion system can further include a sensor for detecting a characteristic of advancement of the plunger within the barrel. The sensor can be a force sensor and/or a flow sensor. The vibration device can be programmed to applying mechanical vibration between the barrel and the plunger in response to detection of the characteristic. The characteristic can indicate when advancement of the drive head does not result in advancement of the plunger within the barrel. The vibration device can be connected to the plunger or the barrel.

A method can include: advancing a plunger of a syringe within a barrel of the syringe at a first rate of advancement, the plunger having a stopper; detecting when friction between the stopper and the barrel exceeds a threshold; and applying mechanical vibration between the barrel and the plunger.

The advancing can be by a drive head. The detecting can include measuring a force between the plunger and the drive head. The detecting can include measuring a flow from the syringe and/or by a motion sensor. The mechanical vibration can be applied to the plunger or the barrel.

A method can include: advancing a plunger of a syringe within a barrel of the syringe at a first rate of advancement, the plunger having a stopper; detecting when friction between the stopper and the barrel exceeds a threshold; modifying, from the first rate of advancement, advancement of the plunger within the barrel for a period of time in response to the detecting.

The modifying comprises: advancing the plunger within the barrel at a second rate of advancement, higher than the first rate; and advancing the plunger within the barrel at a third rate of advancement, lower than the first rate. A combined rate of the second rate and the third rate can be equal to the first rate. The advancing can be by a drive head. The detecting can include measuring a force between the plunger and the drive head.

An infusion system can include: a receptacle for receiving a syringe, the syringe comprising a barrel and a plunger, the plunger having a stopper; a drive head for advancing the plunger within the barrel; and a controller programmed to modify advancement of the plunger within the barrel for a period of time in response to friction between the stopper and the barrel exceeding a threshold.

The controller can be programmed to effect: when friction between the stopper and the barrel does not exceed the threshold, advancing the plunger within the barrel at a first rate of advancement; and when friction between the stopper and the barrel exceeds the threshold, (1) advancing the plunger within the barrel at a second rate of advancement, higher than the first rate and (2) advancing the plunger within the barrel at a third rate of advancement, lower than the first rate. The infusion system can further include a sensor for detecting a characteristic of the advancement of the plunger within the barrel. The sensor can be a force sensor, flow sensor, and/or a motion sensor.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

DETAILED DESCRIPTION

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

Syringe pumps can be used for the infusion of medical fluids, such as parenteral fluids, into the human body. In many cases, smooth delivery of medical fluids is desired. For example, where the medical fluid includes a medication, delivery at a consistent or predicable flow rate allows a medical professional to properly plan and execute a treatment. Mechanical interactions between parts of an infusion system can produce resistance to smooth delivery. Aspects of the embodiments discloses herein address these concerns to provide more consistent and predictable flow during driver operation.

Prompt, continuous, and smooth delivery is also desirable so that treatment can be administered without any unintended delay. For example, medications can be subject to a biological or terminal half-life, in which a span of time is defined for half of the dose to be eliminated from the bloodstream. Accordingly, ensuring that the medication is delivered within an expected time span allows a healthcare provider to deliver an effective dosage. Additionally, low flow rates may be needed for some patients, such as infants. Where a low flow rate is achieved with slow drive head motion, any delay in initial delivery can be amplified by the programmed slow movement of the drive head.

The present disclosure presents multiple aspects that, individually or in combination, can improve systems that include a pump driver and syringe to deliver medication smoothly and promptly at low flow rates.

Figure 1:
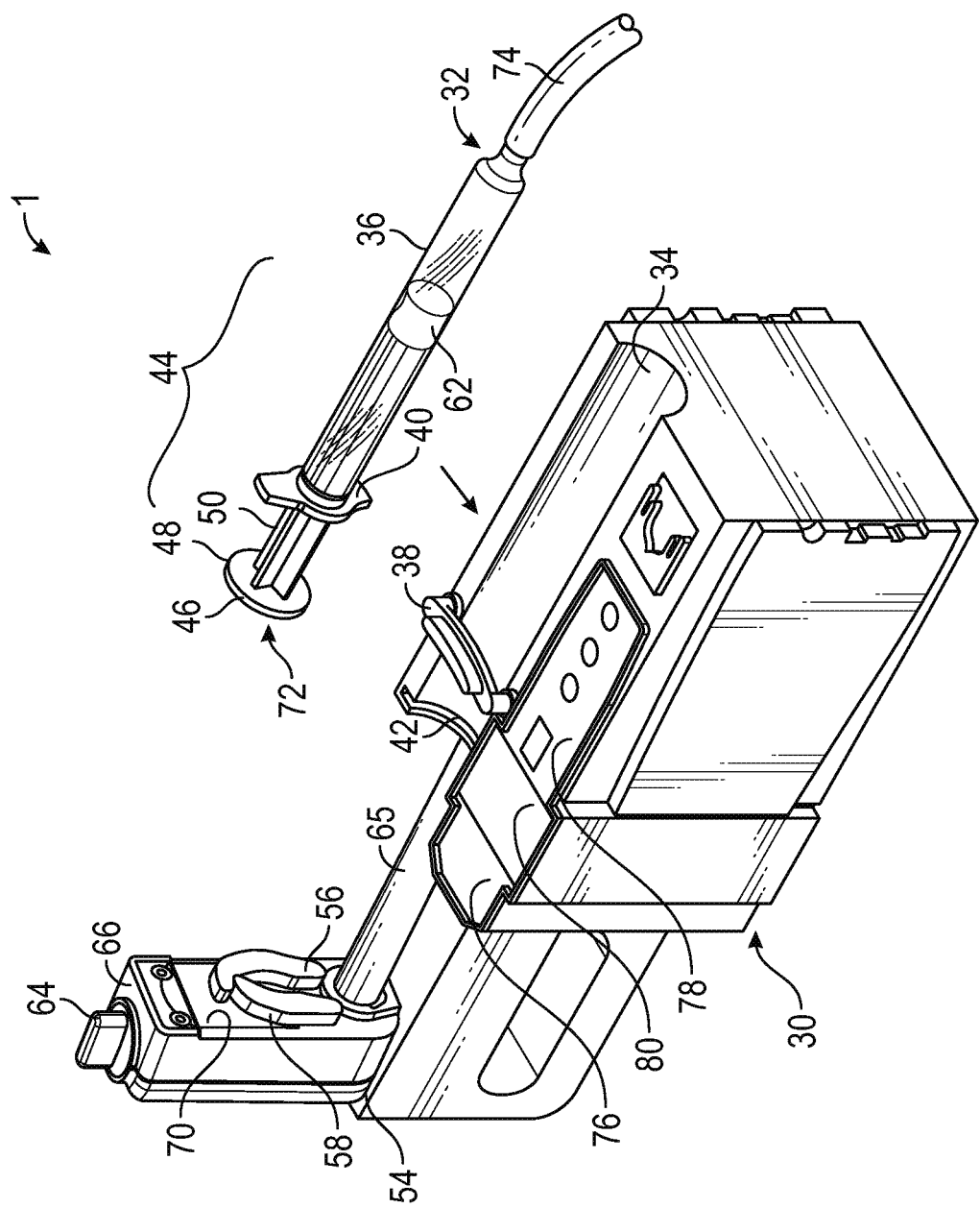
FIG. 1 shows a perspective view of an infusion system including a syringe pump and a syringe, according to some embodiments of the present disclosure.

According to some embodiments, for example as shown in FIG. 1, an infusion system 1 can include a syringe pump 30 having a drivetrain subsystem. A syringe 32 is shown next to the pump rather than mounted in the pump, for clarity of illustration. The syringe pump 30 includes a cradle 34 in which a barrel 36 can rest when mounted in the syringe pump 30. The cradle 34 can include a clamp 38 to securely hold the barrel 36 in a fixed position in the cradle 34 so that axial and lateral movement is resisted. The clamp 38 can be pivoted so that it may be moved into an open position to permit loading or removal of the syringe 32 and a closed position in which it extends over the cradle 34 to hold a mounted barrel 36. A barrel flange 40 of the syringe 32 can be located in a barrel flange groove 42 in the syringe pump 30 to immobilize the barrel 36 from axial movement during movement of the plunger 44 within the barrel 36.

The syringe 32 can include the barrel 36 and the plunger 44. The plunger 44 can include a push-button 46 having an inner side 48 and being interconnected with a stopper 62 of the plunger 44 by a piston 50. The plunger 44 can include the stopper 62 to sealingly engage an inner wall of the barrel 36 to prevent fluid from leaking past the stopper 62. When mounted in the syringe pump 30, the push-button 46 can be held by the drive head 54 with a plunger retainer comprising a pair of pivotally mounted claws, first retainer claw 56 and second retainer claw 58, shown in the closed position in FIG. 1. The retainer claws 56 and 58 can curve inwardly toward each other to grasp a push-button 46 mounted in the syringe pump 30. A rotation knob 64 can be used to control the positions of the first and second retainer claws 56 and 58 to allow removal and insertion of the push-button 46 and to release the split-nut from the driveshaft to permit axial positioning of the drive head 54. Syringes can be provided for use with a syringe pump with different quantities of fluid, and the plunger can be located at different positions in relation to the barrel.

The drive head 54 can allow manual adjustment to accommodate syringes with different beginning plunger positions. A syringe inserted in the cradle 34 can align with the drive head 54 within a particular axial range. The points where the axial center lines of the syringes intersect the driver can change according to the size of the syringe but only in one direction along the drive head 54. A guide device 65 can extend from the drive head 54 to a point within a body of the syringe pump 30.

The pump 30 can include a control panel 76 providing multiple buttons 78 for control of the pump 30 as well as a display 80 used to present pump-specific information to the operator. The buttons 78 can allow the operator to program the pump 30 for the flow rate, the volume to be infused, and other pump parameters. The display 80 can present the programmed flow rate, the amount of fluid remaining to be infused, as well as alarms and other information.

Figure 3:
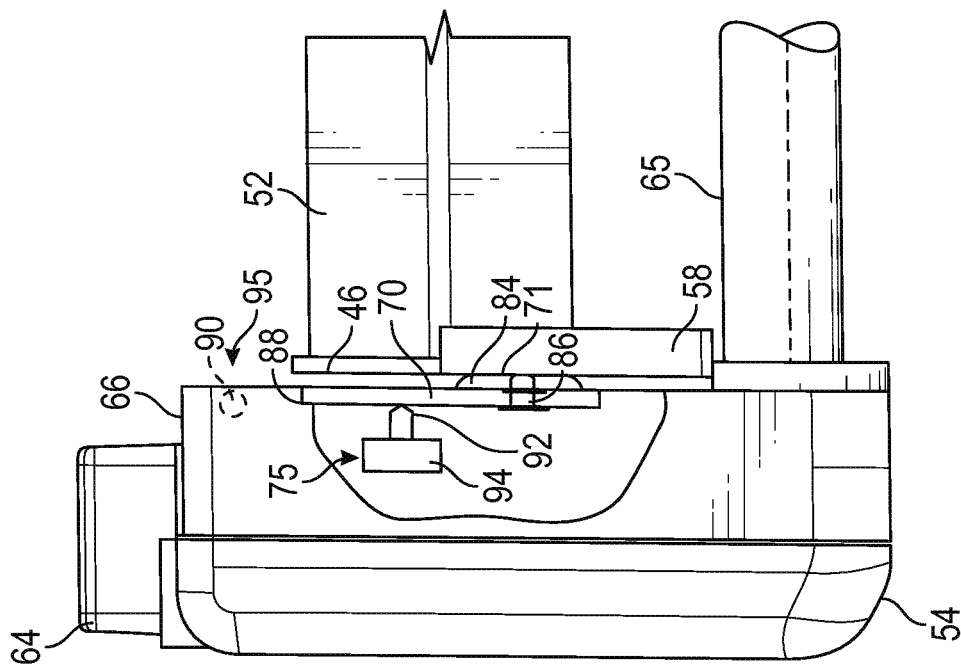
FIG. 3 shows a partial cross-sectional side view of the drive head of the syringe pump of FIG. 1 with the syringe of FIG. 1, according to some embodiments of the present disclosure.
Figure 2:
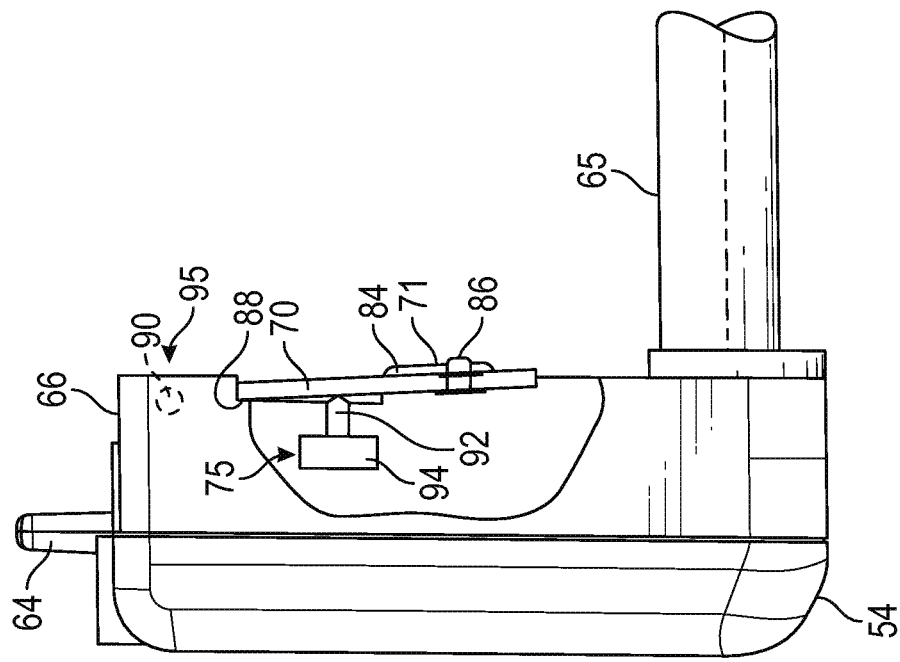
FIG. 2 shows a partial cross-sectional side view of the drive head of the syringe pump of FIG. 1, according to some embodiments of the present disclosure.

According to some embodiments, for example as shown in FIGS. 2 and 3, the drive head 54 can include a contact plate 70 that has a pushing surface 71 that contacts the outer side 72 of the push-button 46 as the drive head 54 moves forward toward the barrel 36, pushing the plunger 44 into the barrel 36 of the syringe to expel the syringe contents through a fluid administration set tubing 74 to the patient. The contact plate 70 can be interconnected to a force sensor system 75. When the contact plate 70 exerts force against the push-button 46, the force sensor 94 reports the detected force, as discussed further herein. A recess 88 can be formed in the drive head 54 to accommodate the contact plate 70. The contact plate 70 can be attached to the drive head 54 inside recess 88 at a pivot point 90. The contact plate 70 can be forced to protrude slightly outward in the vertical direction from the surface of the drive head 54 toward a mounted push-button due to a bias exerted against the push-button contact plate 70 by an extension piece 92 that is coupled to a force sensor 94 located inside the drive head 54. As the pushing surface 71 of the force concentrator 84 of the contact plate 70 exerts a force against the push-button, the force sensor 94 detects the force through the extension piece 92 and transmits the sensed force to a processor for monitoring, as described further herein in relation to FIG. 5. In use, a force exerted by the pushing surface 71 of the force concentrator 84 of the movable contact plate 70 when driving a plunger causes the extension piece 92 to communicate the driving force to the force sensor 94. In the case of friction between the stopper 62 and the barrel 36, the force exerted on the force concentrator 84 can increase and can be sensed by the force sensor 94.

Figure 4:
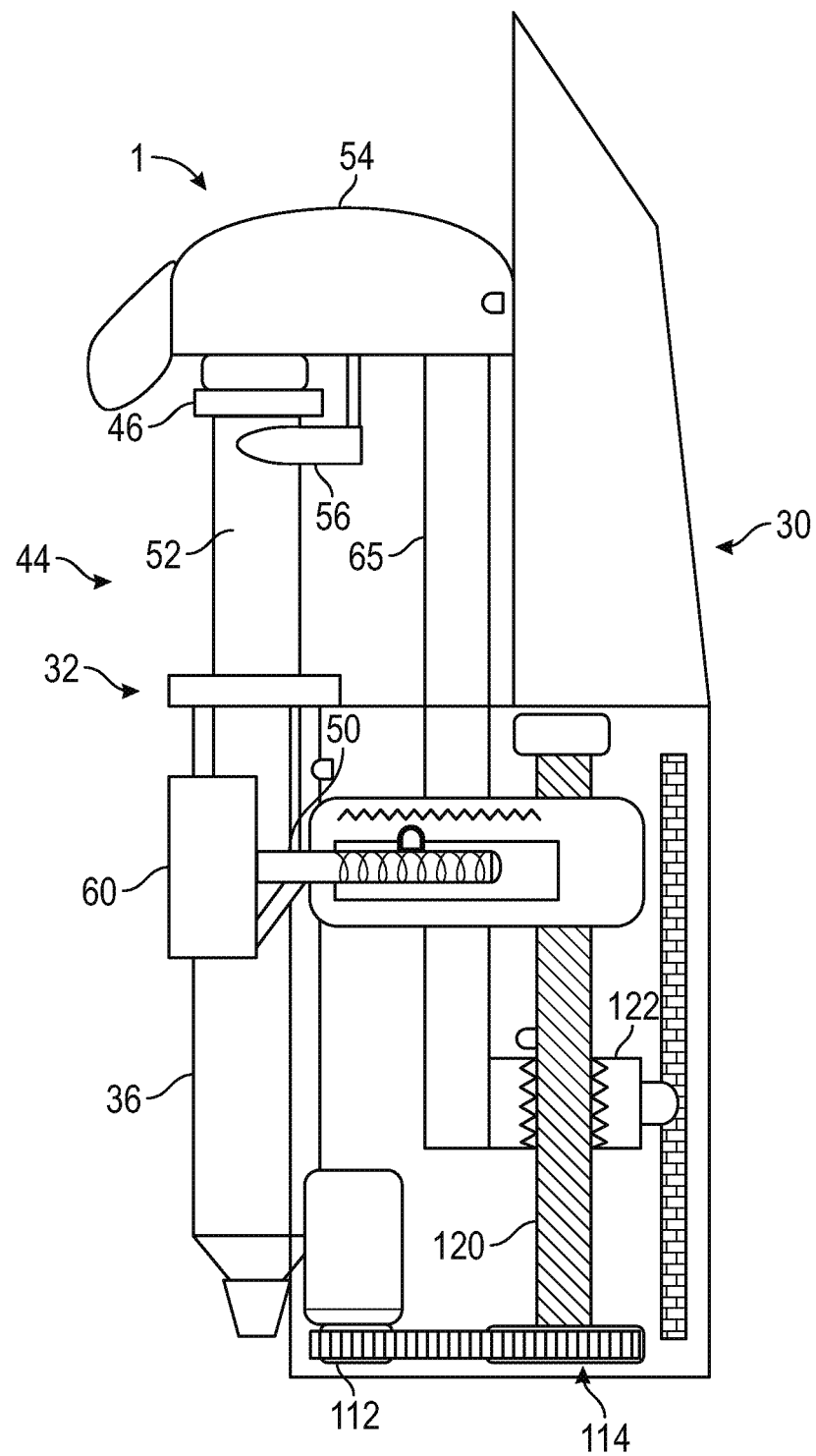
FIG. 4 shows a schematic view of the syringe pump of FIG. 1, according to some embodiments of the present disclosure.

According to some embodiments, for example as shown in FIG. 4, the system 1 can include components for controlling advancement of the plunger 44 within the barrel 36 of the syringe 32. The drive head 54, which engages the push-button 46 of the syringe 32, can be moved by a drivetrain 114 of the pump 30. For example, the pump 30 can include a motor 112 that operates to rotate a lead screw 120. The lead screw 120 is engaged by a screw drive mechanism 122, such as a split nut, that translates the rotational motion of the lead screw 120 into linear motion. The drive head 54 is connected to the screw drive mechanism 122 and to the plunger 44 for driving the plunger 44 into the barrel 36 in accordance with the movement of the lead screw 120 to expel fluid from the barrel 36.

According to some embodiments, the motor 112 can include a stepper motor, a brushed DC electric motor, a brushless DC electric motor, a servo motor, an AC motor, or another type of motor. The drivetrain 114 can include appropriate gears, axles, shafts, chains, hydraulics, and/or any other components for translating rotational motion of the motor 112 into linear motion of the drive head 54. According to some embodiments, the drivetrain 114, including the motor 112, can include linear actuating components, such as a linear stepper motor. For example, a linear motor can act directly on the drive head 54, or a component attached thereto, to control linear motion thereof.

According to some embodiments, for example as shown in FIG. 4, the infusion system 1 can include a vibration device 60 that is coupled to the barrel 36 and/or the plunger 44. The vibration device 60 can include any component that transmits vibrations and/or oscillations into a structure. For example, the vibration device 60 can include a haptic device, a voice coil, a linear resonant actuator, a rotating motor with an eccentric mass, a piezoelectrirc actuator, or combinations thereof. The vibration device 60 can be in contact with the barrel 36 and/or the plunger 44, such that operation of the vibration device 60 transmits vibrations and/or oscillations into the barrel 36 and/or the plunger 44, as discussed further herein. The vibration inducing device can include the primary driveshaft motor itself as well.

Figure 5:
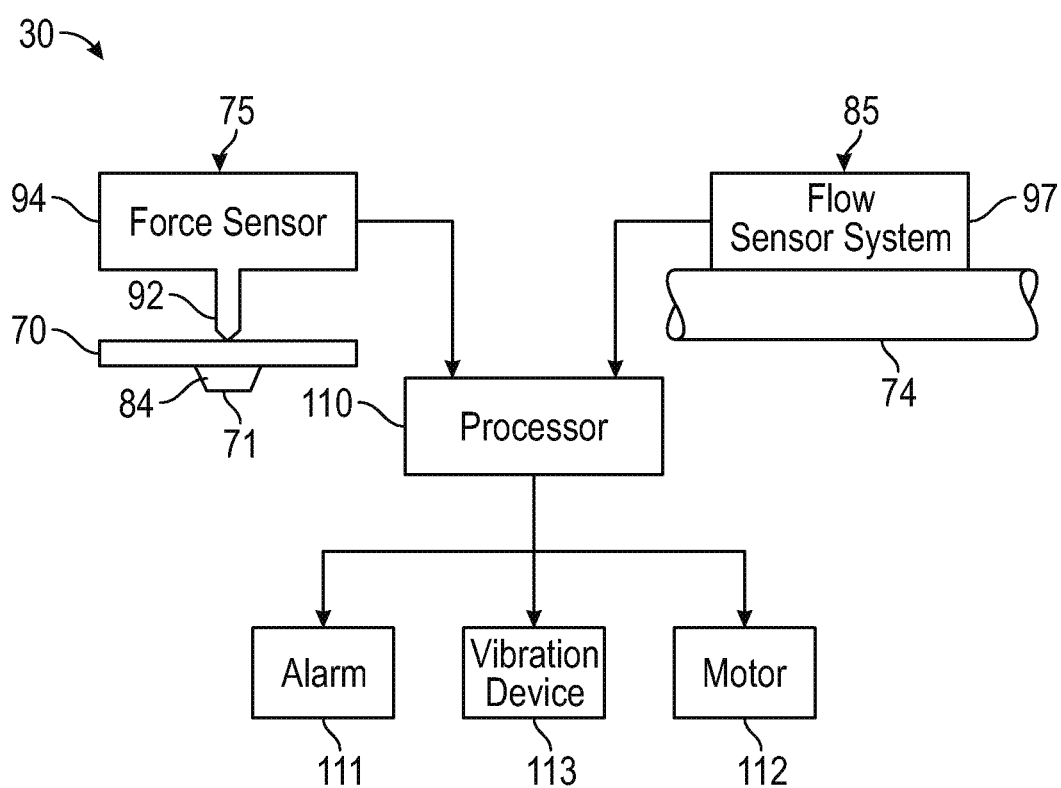
FIG. 5 shows a block diagram showing controller of the syringe pump of FIG. 1, according to some embodiments of the present disclosure.

According to some embodiments, for example as shown in FIG. 5, the syringe pump 30 can include a processor 110 that controls various aspects of operation. The processor 110 can be connected either directly or indirectly to the force sensor 94 and to the flow sensor system 85. The flow sensor system 85 can include one or more sensors 97, such as a force sensor, a displacement sensor, a pressure sensor, and/or a flow sensor. Based on the signals received from these devices and/or other signals, the processor 110 can control the movement of the drive head 54. Conversion equipment, such as analog-to-digital converters, can be provided between the processor 110 and the flow sensor system 85 and/or the force sensor system 75. The processor 110 can connect to a user interface (not shown)

For example, the force sensor 94 can detect a force from the extension piece 92 and output a force signal to the processor 110. The processor 110 can provide a control signal to the motor 112 to control operation of the motor 112. Alternatively or in combination, the processor 110 can provide a vibration signal to a vibration device 113 to control vibration of the components of the syringe 32. Alternatively or in combination, the processor 110 can provide an alarm signal to activate an alarm 111.

Figure 6:
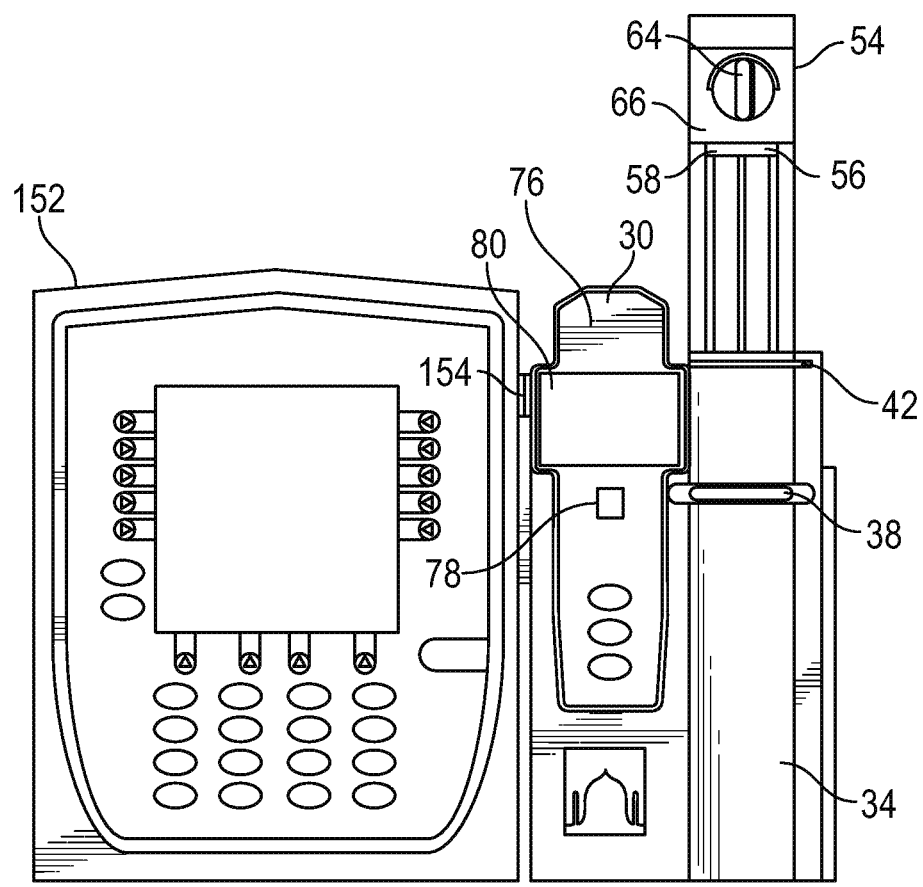
FIG. 6 shows a view of the syringe pump of FIG. 1 mounted to a programming module, according to some embodiments of the present disclosure.

According to some embodiments, for example as shown in FIG. 6, the syringe pump 30 can be mounted to a programming module 152, together forming a modular patient care system. The programming module 152 in FIG. 6 can perform various functions for the pump such as programming and communications. Control elements and functions can be included with and performed, at least in part, by the programming module 152. In addition to the syringe pump 30 mounted to the programming module 152, other modules, such as those providing patient monitoring or therapies, can also form part of the patient care system. The programming module 152 can provide a centralized interface for the various attached modules. One or more syringe pumps can be mounted to the programming module 152 and/or each other.

The drive head 54 can interact with the syringe 32 in a manner that facilitates prompt, consistent, and predicable infusion of a fluid from the syringe 32 to the patient. The features described herein can be used individually or in combination to improve the ability of the system 1 to deliver medication promptly and smoothly at low flow rates.

Drivetrain Stiffness

According to some embodiments, components of the drivetrain 114 can provide sufficient stiffness to facilitate responsiveness of the syringe to activity of the drivetrain 114. Prior systems permit significant flexibility in the drive 114 that is used to displace a plunger. Friction can occur between the stopper 62 of the piston 50 and the inner wall of the barrel 36. As the drive head 54 attempts to apply a displacement to the plunger 44, the friction of the stopper 62 will apply an opposing force. Where the drivetrain 114 contains flexible components, little or no motion of the plunger 44 can occur until the drivetrain 114 has compressed enough to overcome the friction. Only after such compression does advancement of the plunger 44 commence at the programmed speed. A resulting mean flow rate of the fluid can be determined based on the inner diameter of the barrel 36 and the speed of the plunger 44.

An adequate stiffness (i.e., "spring rate") of the drivetrain 114 pressing on the plunger 44 reduces the time required for flow to commence and concurrently mitigates the occurrence of flow fluctuation over the course of delivery due to "stick-slip" or "stiction." Such stiffness can be achieved by selecting materials and shapes that reduce flexibility in the drivetrain 114. Furthermore, coupling between components of the drivetrain 114 can be optimized to reduce flexibility and slack in the drivetrain 114.

Initial Acceleration After Syringe Installation

According to some embodiments, the drive head 54 can interact in a particular way after initial installation of the syringe 32 to commence infusion. The drive shaft can provide, in selected modes, acceleration intended to take up some or most of the mechanical slack within the drivetrain 114 and the syringe stopper, which is present following installation of the syringe 32 and engagement of the drive head 54. For large syringes (e.g., greater than 30 cc), which can be used for long-term continuous infusion of short half-life medications, the accelerated movement can be increased to avoid a delay in the onset of flow. The additional accelerated movement is provided to the larger syringe sizes due to the significant thickness of a flexible (e.g., rubber) stopper of the piston 50 between rigid portions of the plunger 44 and the wall of the barrel 36. This material of the stopper may stretch significantly prior to the commencement of movement at the barrel wall interface. Thus, little or no fluid may flow for some time even though the drive head 54 and the piston 50 of the plunger 44 is moving.

The accelerated movement can be faster than the nominal speed for the programmed flow rate to overcome slack within the drive system as well as the stretching of the stopper between the barrel wall and the plunger head. Where the drive head 54 is programmed to advance at a nominal speed during regular infusion, the drive head 54 can be further programmed to advance at an initial speed prior to regular infusion. The initial speed can be greater than the nominal speed. The drive head 54 can be programmed to advance at the initial speed upon confirmation that the syringe 32 is loaded. The drive head 54 can be programmed to transition to the nominal speed after a span of time, after traveling a distance, of upon confirmation of a detectable condition, such as a force between the drive head 54 and the plunger 44. The nominal speed can be bounded by experimentally determined and/or clinically relevant maxima. The initial speed can be applied at the beginning of any infusion and controlled, for example with feedback, based on the force detected at the drive head.

The movement rate and amount can be tuned to specific syringe designs. The pump can recognize the syringe size by automated detection and/or by manual input. Based on this information, the pump permits pre-stored constants to be used to optimize the acceleration phase for specific syringes. Each syringe can have a different response to the initial speed and the nominal speed. Syringe factors which govern initial speed include compliance, friction, and flexure of the piston. Given these factors, the pump can change the exact initial speed profile to optimize the time to flow start. Corresponding characterizations can be determined for individual syringes and/or based on particular syringe features that can be common across multiple syringes.

In some syringe pumps, following initiation of infusion (Start function), an initial motion is produced by a number of motor steps (e.g., 4,000 motor steps, or 0.25 mm). Following activation of a Start function, the drive shaft is optionally advanced up to a pre-determined distance (e.g. 0.25 mm). The total motion may be reduced upon detection of certain conditions, such as when a force of the drive head on the plunger increases by more than a fixed amount or percent or the in-line sensed pressure increases similarly. This type of accelerated movement can still lead to a delayed start of flow, and therefore have an undesirable clinical impact. It may also produce undesired excess initial flow.

According to some embodiments of the present disclosure, additional abilities can be provided to a syringe pump. During operation, details of an acceleration movement can be measured, and operation can be adapted based on monitoring of inline fluid flow, pressure, and/or piston forces. Adaptive acceleration can move the drive head 54 forward quickly during an initial stage (e.g., first few tenths of a mm of movement) to overcome slack, such as in the drivetrain 114 and in the syringe 32 (e.g., stopper-to-barrel interface).

Figure 7:
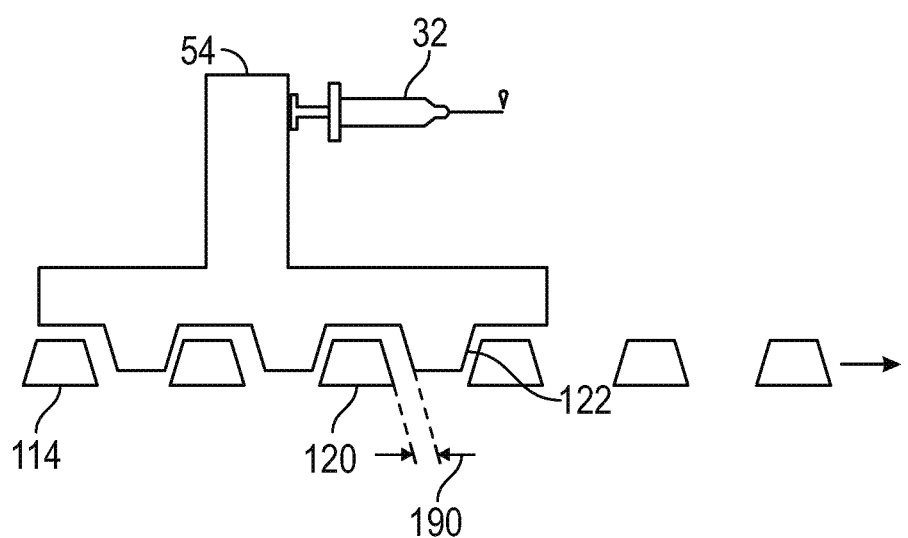
FIG. 7 shows a schematic view of a driveshaft and coupling of a syringe pump and syringe, according to some embodiments of the present disclosure.

According to some embodiments, an initial stage of operation can be used to predict how much movement of the motor is required to avoid a delay attaining the steady state target flow. Experimental results of an exemplary embodiment are shown in FIGS. 7-11. For example, FIG. 7 shows a schematic representation of the drivetrain 114 for interaction with the syringe 32. The drivetrain 114 can include, for example, the lead screw 120 engaged by the screw drive mechanism 122, such as a split nut. A gap 190 in the drivetrain 114 can represent slack in the drivetrain 114, such as between the lead screw 120 and the screw drive mechanism 122. As described herein, the gap 190 must be closed before the syringe is actuated to cause fluid to flow from the syringe.

In the experiment performed using a commercially available Alaris 7110 pump, during approximately an initial span of time (e.g., 4 seconds) after activation commences, an optional "dither" operation causes a stepper motor to advance a first distance (e.g., 4,000-8,000 steps or 0.25-0.5 mm), then retract a second distance (e.g., 8,000-16,000 steps or 0.5-1.0 mm), and finally advance a third distance (e.g., 4,000-8,000 steps or 0.25-0.5 mm). This "dither" operation can be done to ensure engagement of the half-nut of the drive head assembly with the main drive shaft teeth. The expectation is that the net movement across the operation returns the drive head to its original position, thereby not producing any flow. Accordingly, the degree and direction of first, second, and third distances can have a combined net distance of zero. For example, the sum of the first and third distances can be equal to the second distance, and the travel for the second distance can be in a direction that is opposite the direction travelled for the first and third distances. The rapid initial movement can at least temporarily eliminate any residual gap left when the user releases the head clamp and engages the split nut. This variation in gap may be present initially since a push-button can be anywhere along the axis of the drive head but the gear engagement may only occur each integral value of the drive shaft (1/20 inch=about 1.2 mm). However, when the shaft returns to where it began, the gap can again be present.

Figure 8:
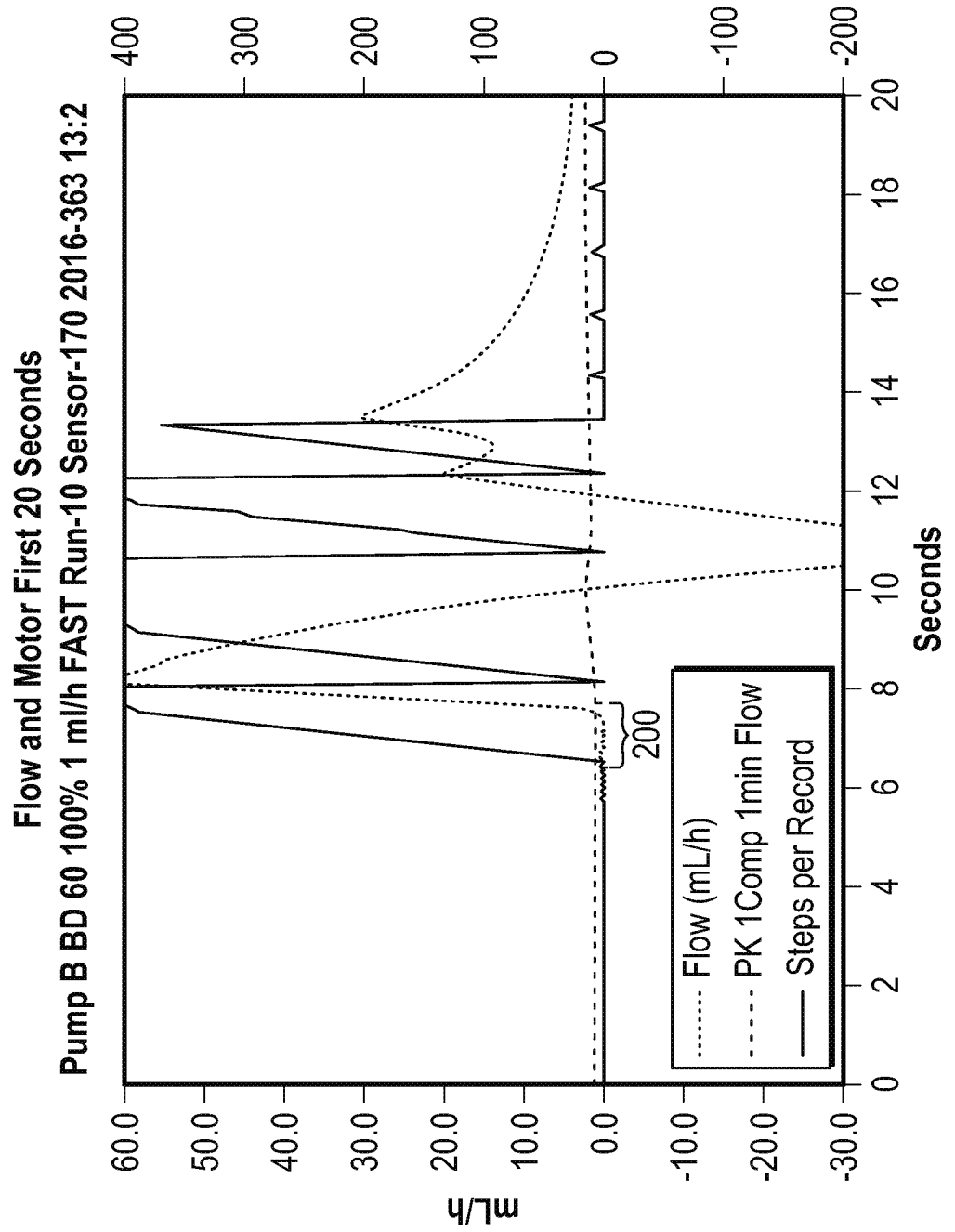
FIG. 8 shows experimental results of a multi-stage syringe driver procedure in which, according to some embodiments of the present disclosure.
Figure 9:
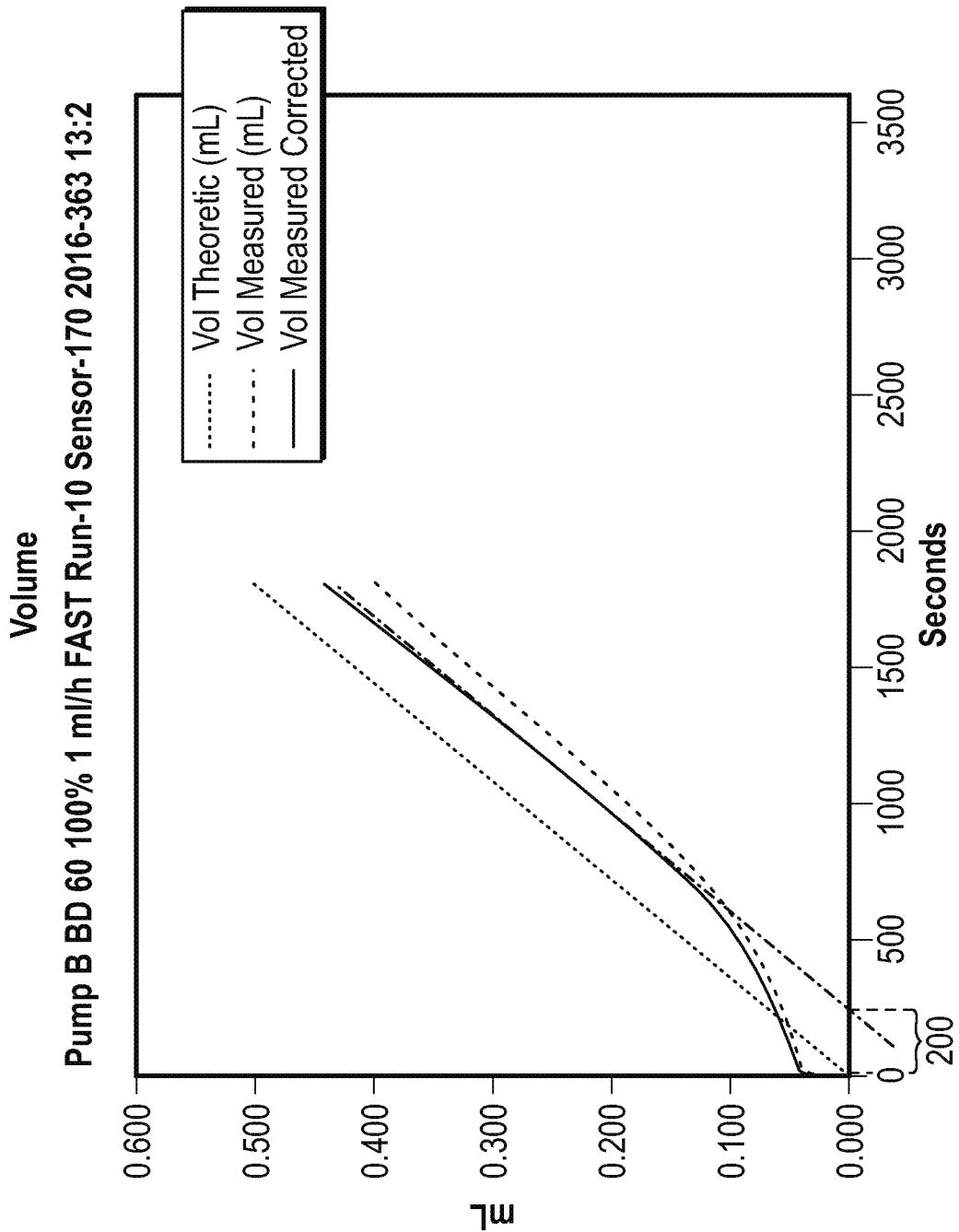
FIG. 9 shows experimental results of a multi-stage syringe driver procedure, according to some embodiments of the present disclosure.
Figure 10:
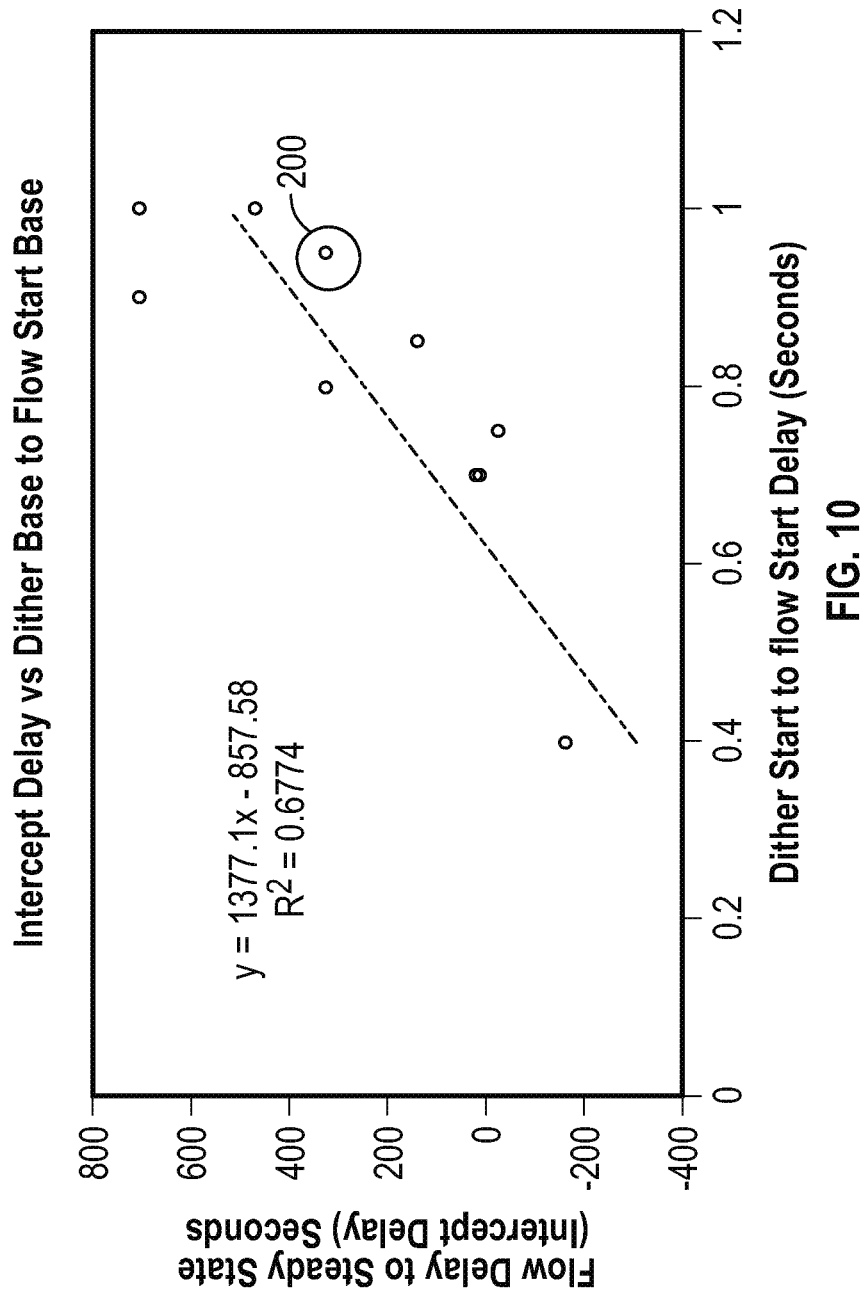
FIG. 10 shows experimental results of multiple procedures, according to some embodiments of the present disclosure.

As shown in FIG. 8, after the forward dither movements begin, a brief pulse of flow can be generated, for example during the initial stage 200 (initial positive flow values in FIG. 8). Subsequently, the flow can reverse (negative flow values in FIG. 8) and then be restored (final positive flow values in FIG. 8). During the initial stage 200, a span of time can pass before the flow reaches a steady state. In the initial stage 200, operation of the motor does not directly correspond to resultant flow due to, for example, slack or gaps in the drivetrain. In the steady state, operation of the motor can directly correspond to resultant flow. As shown in FIG. 9, the theoretic and measured volumes of flow are shown with respect to time. The theoretic volumes of flow can be based on motor operation and/or drive head advancement. As shown in FIG. 10, a study of several runs showed a good correlation between the initial very short time delay (e.g., during a "dither" operation) and the subsequent long delay during normal operation.

Figure 11:
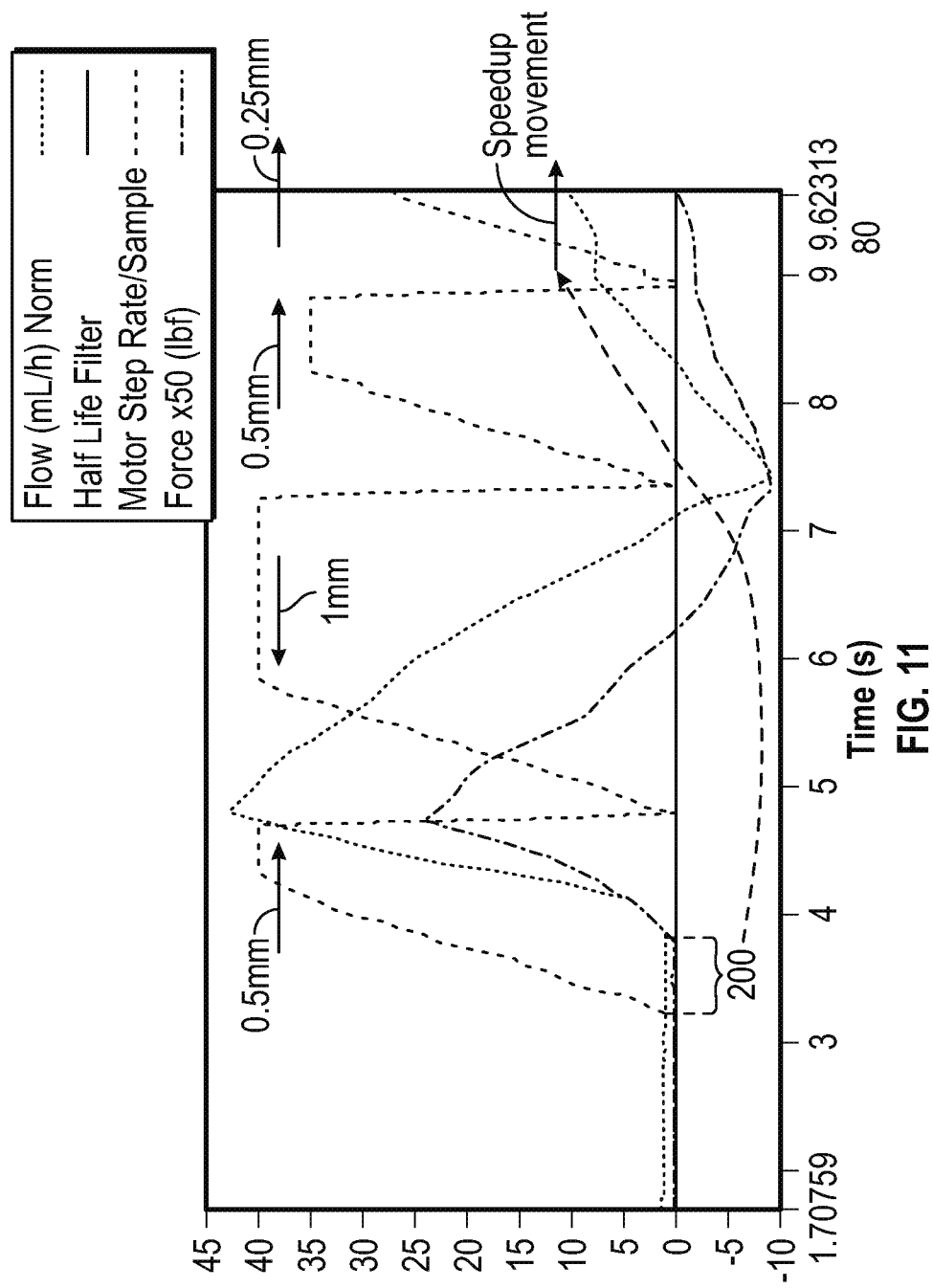
FIG. 11 shows experimental results of a multi-stage syringe driver procedure, according to some embodiments of the present disclosure.

It will be understood that, in some embodiments of the present disclosure, the drive system does not require or utilize dither movements as described herein. Thus, the time or distance measured between initial driveshaft movement and detection of the force, flow, or fluid pressure increase would not involve any of the dither actions described above. Where the dither actions are applied, a method utilizing the initial stage operations would measure the "initial delay" during the first forward phase of dither. While FIGS. 8-10 show flow as the measurement, additional experimental results have demonstrated that force between the drive head and the plunger can also indicate productive flow. As shown in FIG. 11, the flow commences along with forces above a threshold. Accordingly, measuring the delay between motor start and initial onset of force can provide an effective predictor of the number of additional steps for which the motor should run in a fourth and final preliminary movement stage.

By predicting an accurate required number of Speedup Steps based on each specific loading, size of syringe and time or number of steps from onset of net forward motion of the driveshaft until detection of flow or a surrogate (force or pressure rise), and ensuring they will always be executed, the delay in attaining steady state flow will be reduced or eliminated safely.

Driver Movements to Reduce Flow Fluctuation

As described above, a drive head 54 can be operated by a drivetrain 114 that includes a motor 112, such as a stepper motor coupled to a gear reduction system and a drive shaft. Some systems implementing a motor impart fine motions to a drive head in an attempt to achieve smooth flow out of a driven syringe. The motions can include advancement by many small increments. However, for some large syringes, moving the plunger at slow speeds permits a stopper (e.g., rubber) of the plunger to adhere to the wall of the barrel, thereby establishing a requirement that a larger force be required to break free and transition from static to dynamic friction. With each transition from static to dynamic friction, the flow is initially slow and subsequently experiences rapid acceleration.

According to some embodiments, the drive head 54 can be advanced at a variable rate to reduce the smoothness of drive movement and reduce the amplitude of a stiction pattern. The variable rate can reduce static friction between the stopper 62 and the barrel 36 for a greater proportion of time than occurs with a more constant rate of advancement. While this approach can introduce some periodic variation, it can be controlled to be appropriate for the conditions of delivery, such as drug behavior as well as syringe properties. The overall result across several cycles is a pattern of flow that is more regular than could be achieved ordinarily since the large buildup of elastic energy is avoided by dissipation in small quanta.

The drive head 54 can be advanced in one of at least two modes. In a first mode, the drive head 54 can be moved with finer increments of advancement. The increments can be evenly distributed across time to achieve a resultant flow from the syringe 32. As the drive head 54 acts on the plunger 44, the force sensor 94 can detect the force between the drive head 54 and the plunger 44. When friction between the stopper 62 and the barrel 36 increases, the force required from the drive head 54 to move the plunger 44 can correspondingly increase. As such, the force required to move the plunger 44 can be detected by the force sensor 94. Alternatively or in combination, a flow sensor can be provided at an outlet (e.g., tubing 74) of the syringe 32 to detect flow. When the drive head 54 applies a force and the resulting flow does not correspond to the expected amount of flow, the system can detect that the plunger 44 has not advanced as expected in response to the drive head 54. By one or more of the methods described herein, the system can detect the presence of friction and commence a second mode. In the second mode, the drive head 54 can be moved with coarser movements and/or with bursts of multiple consecutive incremental movements in a shorter period of time than would be provided in the first mode. After any one of the bursts of movements, the system can suspend movement of the drive head 54, such that the average rate of advancement or infusion in the second mode is the same or substantially the same as the rate of advancement or infusion in the first mode. During the bursts of movement, the static friction can be avoided by maintaining dynamic motion of the plunger 44 (e.g., including stopper 62) relative to the barrel 36. While static friction may occur between bursts, the overall occurrence rate is reduced because the static friction does not occur for as many increments of movement. Thus, the system applying these modes of operation provides dynamic and adaptive alteration of movement patterns to reduce the presence of static friction.

Mechanical Vibration

The formation of dynamic and static friction fluctuations between plunger 44 and the barrel 36 can cause both slow commencement of flow as well as variation of flow due to stiction. Mechanical vibrations and/or oscillations through the barrel 36 and/or the plunger 44 can maintain continual relative motion to inhibit formation of the high force static friction state.

As discussed above, the infusion system 1 can include a vibration device 60 that is coupled to the barrel 36 and/or the plunger 44. The vibration device 60 can be in contact with the barrel 36 and/or the plunger 44, such that operation of the vibration device 60 transmits vibrations and/or oscillations into the barrel 36 and/or the plunger 44. As a result, the plunger 44 and the barrel 36 are moved relative to each other on a small scale for a period of time. The vibrations and/or oscillations can relieve a static friction between the barrel 36 and the stopper 62.

The vibration device 60 can operate a given frequency, amplitude, and duration of time. For example, the vibration device 60 can be operated prior to, during, and/or after the drive head 54 applies a force to the plunger 44. Where friction is detected by the system (e.g., by the force sensor 94 and/or a flow sensor) the vibration device 60 can be operated in response to the detection of friction.

Some embodiments of the present disclosure can include one or more of the features discussed herein. For example, some embodiments can include one, some or all of a stiff drivetrain, initial acceleration after syringe installation, drive head movements to reduce flow fluctuation, and/or mechanical vibration. Any of the various features disclosed herein, individually or in combination, can increase promptness and consistency of fluid delivery. Features can cooperate collectively to produce the desired rapid commencement of flow followed by smooth delivery uninterrupted by stiction-induced slowing and acceleration. For example, a stiffer drivetrain can reduce the time required to build drive head force and liquid pressure to an alarm level during a blockage of the outflow path. The motor drive, gearing, and control parameters can enable customized acceleration patterns which may be specific to selected syringe size, brand and model. These patterns can minimize or eliminate the delay in commencement of flow by overcoming both mechanical slack remaining and syringe stopper slack. To avoid flow irregularities produced by stiction forces in the stopper further, the mechanical vibration can be coupled to the syringe and/or barrel to introduce movement of the stopper-wall interface, reducing the creation of high static friction coefficients. Increased stiffness can also reduce the time required to detect occlusion.

Method

Figure 12:
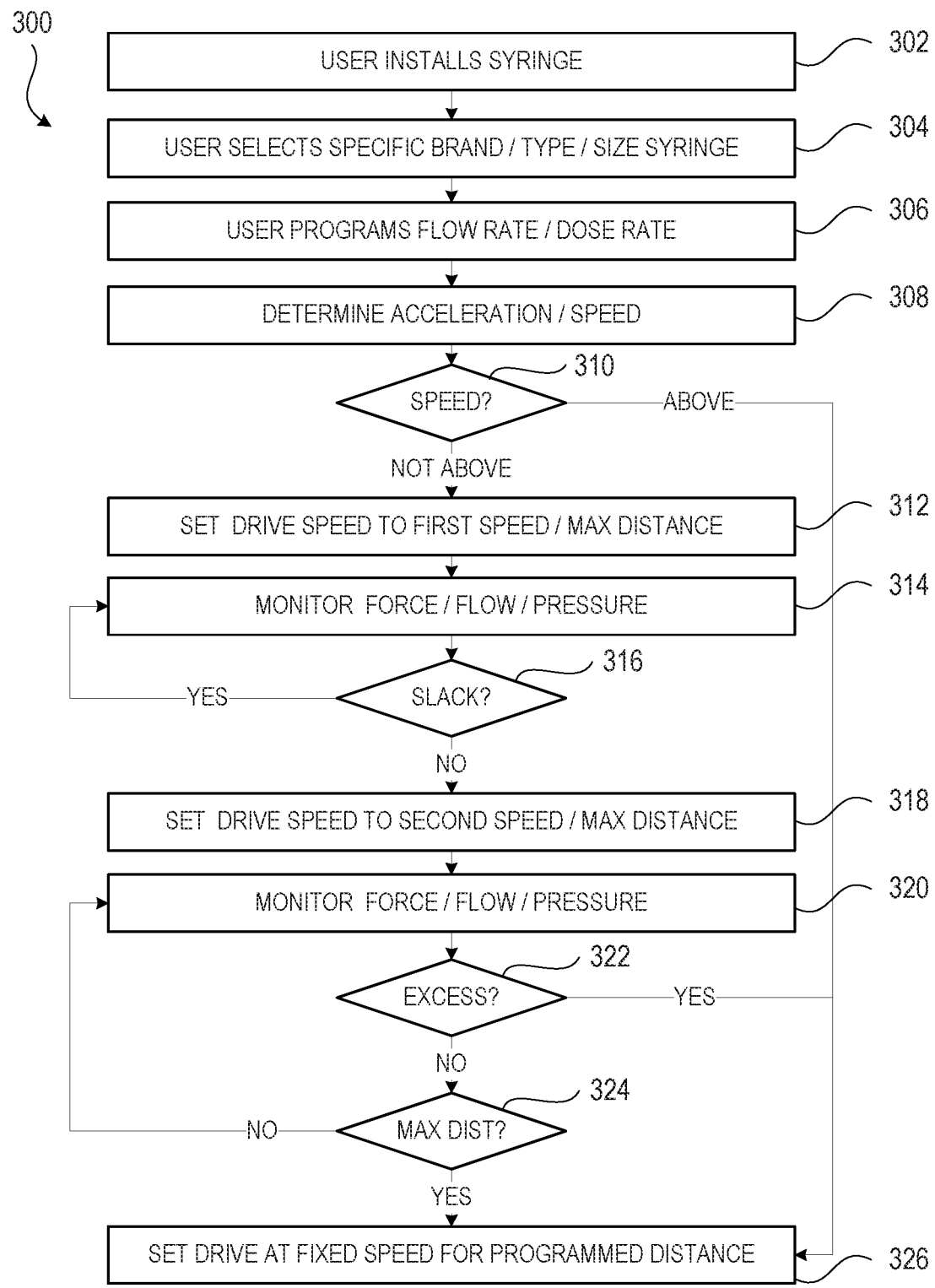
FIG. 12 shows a flow chart of a method for controlling a drive mechanism, according to some embodiments of the present disclosure.

As shown in FIG. 12, a method 300 can be performed according to the embodiments disclosed herein. The method 300 can be used to control the speed, distance, and/or other parameters of the drive mechanism.

In operation 302, a user can install a syringe, as discussed above. In operation 304, the user can provide properties of the syringe as an input for a control system. The properties can include brand, type, size, or other information that can be used to identify or characterize the syringe. The information can optionally be used by the control system to reference further information (e.g., from a database) relating to the syringe. In operation 306, the user can provide one or more operational parameters. The operational parameters can include flow rate, dose rate, or other information that can be used to determine operational parameters. For example, flow rate, dose rate, and/or driver speed can each be provided by a user and/or calculated based on other information provided by a user or programmed into the control system.

The user and/or another system can start a procedure executed by the control system. Additionally or alternatively, the process can be initiated automatically and/or based on other inputs (e.g., remote control or time delay). In operation 308, the system monitors, measures, or otherwise determines acceleration and/or speed of the driver based on the syringe and/or flow data. In operation 310, the speed of the driver is compared to a threshold or range. For example, if the acceleration and/or speed of the driver is above a threshold or within a target range, then the driver speed can be set to a final (e.g., fixed or target) speed for a programmed distance, as shown in operation 326. However, if the acceleration and/or speed of the driver is not above a threshold or within a target range, then the driver speed can be set to a first speed for a first distance (e.g., maximum distance), as shown in operation 312.

During operation at the first speed and/or while the driver is within the first distance, the system can monitor, measure, or otherwise determine operational properties, such as forces, flow, and/or pressure, as shown in operation 314. In operation 316, the system can determine whether slack (e.g., a gap) within the drivetrain is present or whether it has been removed. For example, the flow properties can be compared to expected flow properties where no slack is present. Slack can be present between interfaces within the drivetrain. For example, slack can be present between a drive shaft (e.g., lead screw) and screw drive mechanism (e.g., split nut), between a drive head and push-button, and/or between a stopper and a barrel. If the properties indicate that slack is present, then the drive operation can continue based on operations 312 and 314. However, if the properties indicate that slack is present (e.g., that slack has been removed), then the driver speed can be set to a second speed for a second distance (e.g., maximum distance), as shown in operation 318.

During operation at the second speed and/or while the driver is within the second distance, the system can monitor, measure, or otherwise determine operational properties, such as forces, flow, and/or pressure, as shown in operation 320. In operation 322, the system can determine whether excess forces, flow, and/or pressure is present. For example, the forces, flow, and/or pressure can be compared to one or more target values or ranges. If the properties indicate that forces, flow, and/or pressure are excessive (e.g. above a target), then the driver speed can be set to the final (e.g., fixed or target) speed for the programmed distance, as shown in operation 326. However, if the properties indicate that forces, flow, and/or pressure are not excessive (e.g. above a target), then the system can determine whether the driver is within the second maximum distance as shown in operation 324. If the driver has not reached the second maximum distance, then the drive operation can continue based on operations 318 and 320. If the driver has reached or exceeded the second maximum distance, then the driver speed can be set to the final (e.g., fixed or target) speed for the programmed distance, as shown in operation 326. It will be understood that the decisions of operations 322 and 324 can be performed in any order and/or simultaneously.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. An infusion system comprising:
    a modular syringe pump, comprising:
        a receptacle for receiving a syringe, the syringe comprising a barrel and a plunger having a stopper;
        a drive head for advancing the plunger within the barrel, the drive head comprising:
            a recess; and
            a contact plate disposed in the recess, the contact plate configured to engage a push-button of the plunger;
        a drive mechanism coupled to the drive head;
        a drivetrain configured to engage the drive mechanism;
        a vibration device for applying mechanical vibration between the barrel and the plunger;
        a motor configured to dither the drive head, the dithering comprising advancing the motor a first distance, retracting the motor a second distance and advancing the motor a third distance to reduce a gap size between the drivetrain and the drive mechanism; and
    a programming module configured to control and communicate with the syringe pump; and
    a sensor for detecting a characteristic of advancement of the plunger within the barrel, the characteristic indicating a friction between the barrel and the plunger,
    wherein the vibration device is programmed to applying mechanical vibration between the barrel and the plunger in response to detection of the characteristic,
    wherein the modular syringe pump is configured to be one of mounted to the programming module and mounted to another modular syringe pump,
    wherein the programming module is configured to provide a parameter to the modular syringe pump,
    wherein the drive mechanism is configured to operate at a first speed over a first maximum distance of travel of the drive head when a current speed of the drive mechanism is one of not above a threshold speed and not within a target range of speed,
    wherein the drive mechanism is configured to operate at a second speed over a second maximum distance of travel of the drive head when an absence of slack in the drivetrain is indicated,
    wherein the drive mechanism is configured to operate at a third speed over a programmed distance of travel of the drive head when the drive head has traveled the second maximum distance.

2. The infusion system of claim 1, wherein the sensor is a force sensor, a displacement sensor, a pressure sensor, and/or a flow sensor.

3. The infusion system of claim 2, wherein the sensor is a first sensor, the infusion system further comprising:
    a second sensor comprising a flow sensor disposed at an outlet of the syringe, the second sensor configured to detect a flow of fluid at the outlet,
    wherein the vibration device is programmed to applying mechanical vibration between the barrel and the plunger in response to detection of the friction between the barrel and the plunger and the detection of the flow of fluid.

4. The infusion system of claim 3, wherein the detection of the flow of fluid comprises commencement of flow of fluid slower than a set amount.

5. The infusion system of claim 3, wherein the detection of the flow of fluid comprises variation in flow due to stiction.

6. The infusion system of claim 1, wherein the characteristic indicates when advancement of the drive head does not result in advancement of the plunger within the barrel.

7. The infusion system of claim 1, wherein the vibration device is connected to the plunger.

8. The infusion system of claim 1, wherein the vibration device comprises one of a haptic device, a voice coil, a linear resonant actuator, a rotating motor with an eccentric mass and a piezoelectric actuator.

9. The infusion system of claim 1, wherein the motor is operationally coupled to the drive head, wherein the vibration device comprises the motor.

10. The infusion system of claim 1, wherein the vibration device is connected to the plunger and the barrel.

11. The infusion system of claim 1, wherein the vibration device is connected to the barrel.

12. The infusion system of claim 1, wherein the vibration device is configured to apply mechanical vibration between the barrel and the plunger only prior to the drive head applying a force to the plunger.

13. The infusion system of claim 1, wherein the vibration device is configured to apply mechanical vibration between the barrel and the plunger only during the time the drive head applies a force to the plunger.

14. The infusion system of claim 1, wherein the vibration device is configured to apply mechanical vibration between the barrel and the plunger only after the drive head applies a force to the plunger.

15. The infusion system of claim 1, wherein the motor is a stepper motor.

16. The infusion system of claim 1, wherein the dithering is configured to ensure engagement of a half-nut of the drive head with teeth of a main drive shaft by closing a gap between a lead screw of the main drive shaft and the half-nut of the drive head.

17. The infusion system of claim 1, wherein the net movement of the first, second and third distances returns the drive head to its original position and does not produce any fluid flow from the syringe.

18. The infusion system of claim 1, wherein a degree and direction of the first, second and third distances have a combined net distance of zero.

19. The infusion system of claim 1, wherein the first distance is in a range of 0.25 to 0.5 mm, the second distance is in a range of 0.5 to 1.0 mm and the third distance is in a range of 0.25 to 0.5 mm.

20. The infusion system of claim 1, wherein the drive mechanism is configured to operate at the third speed before reaching the second maximum distance of travel of the drive head when a detected operational property is above a target level.

\* \* \* \* \*